United States Patent [19]

Bery

[11] Patent Number: 4,541,273
[45] Date of Patent: Sep. 17, 1985

[54] STRUCTURAL AND SURFACE PROPERTIES TESTER FOR PAPER

[75] Inventor: Yuri A. Bery, Tukwila, Wash.

[73] Assignee: Weyerhaeuser Company, Tacoma, Wash.

[21] Appl. No.: 548,166

[22] Filed: Nov. 2, 1983

[51] Int. Cl.[4] .............................................. G01B 21/30
[52] U.S. Cl. ...................................... 73/150 R; 73/159
[58] Field of Search ................. 73/150 R, 159, 7, 105, 73/78; 118/76; 427/11

[56] References Cited

U.S. PATENT DOCUMENTS

| 257,761 | 5/1882 | Ridgeway | 427/11 |
|---|---|---|---|
| 2,035,220 | 3/1936 | Bramberry | 73/105 |
| 2,353,852 | 7/1944 | Rowland et al. | 73/159 |
| 3,412,605 | 11/1968 | Oehme et al. | 73/150 |
| 3,585,854 | 6/1971 | Hanson | 73/105 |
| 4,068,385 | 1/1978 | Mitzel | 73/159 |

FOREIGN PATENT DOCUMENTS 0684295  9/1979  U.S.S.R. ................................. 73/105

OTHER PUBLICATIONS

J. Marton, GRI Report No., M-102 (1978), p. 327.
O. Kalimes, M/k Systems, Inc., "New Approach to Measuring Formation-A Matter of Uniformity", Paper Trade Journal/Oct. 25, 1971, pp. 46-50.

Primary Examiner—Charles Frankfort
Assistant Examiner—Thomas B. Will

[57] ABSTRACT

A method and apparatus for analyzing the structural formation and surface properties of fibrous sheet materials, particularly printing papers, are described. The method requires advancing a marker over a substantial area of the sheet to be tested. The marker is urged into contact with the sheet so that it exerts a pressure on it, typically of printing process magnitudes. The marker is any material which produces an image the intensity of which is proportional to the pressure exerted upon it by the test sheet. A preferred marker is graphite. The image produced is equivalent to those produced by Beta ray formation analyzers and may be evaluated by a missing dot technique commonly employed in rotogravure print quality evaluations.

22 Claims, 13 Drawing Figures

STRUCTURAL AND SURFACE PROPERTIES TESTER FOR PAPER

BACKGROUND OF THE INVENTION

1. Field of the Invention

The present invention relates to a method and apparatus for evaluating formation and surface characteristics of a fibrous sheet material and predicting its performance in finished articles. In particular, the invention relates to the effects of formation and surface smoothness on the printability of papers.

2. Description of the Prior Art

Evaluating papers manufactured by printing to judge how they are likely to perform in printing is difficult today because of a lack of methods and equipment which reflect what actually happens to papers in printing processes. Those instruments which do reflect printing conditions are too slow or comprise expensive equipment or require skilled persons to operate. What is needed is a printability tester that is fast and simple enough to be used in the mill environment, yet produces results that relate to qualities important in printing.

There are printability testers for evaluating papers which are basically printing presses. Their advantage is that they duplicate the pressure conditions to which a paper is subjected in printing. Conventional printing process such as letterpress, offset, and gravure require physical contact between ink bearing surfaces and the paper being printed. Contact pressures vary depending upon the method employed, but are generally on the order of tens of kilograms per square centimeter. Early workers with printing testers had difficulty in eliminating print differences resulting from an inability to control the amount of ink applied to a test paper. For example, applying too much ink to a printing plate causes difficulties because the ink tends to flow from contact areas into non-contact areas due to wetting forces. Reducing the amount of ink used quickly reaches a limit as the inks become very difficult to transfer uniformly. The result in either case is that quality differences related to the papers can become veiled by the difficulties related to ink transfer.

Some printability tester manufacturers eliminated inking difficulties by selecting the rotogravure printing process. In gravure printing testers, an image is formed on a printing plate by mechanically engraving, or chemically etching a multiplicity of minute dots or cells (30-120 microns in diameter) on a cylindrical printing plate. In printing, each cell is filled with ink and the excess wiped or doctored from the plate. The depth of the cells and their spacing determine the tone produced on the paper.

If a paper fails to contact a cell, no ink will transfer and there will be a skip or missing dot on the resulting print. It is evident that print quality can be judged by the number of missing dots. The gravure process eliminates the non-uniformity of ink transfer problem. Where the gravure tester is otherwise designed to ensure that the only test variable remaining is the paper itself, missing dot count is a measure of gravure printability of a given paper. It has been found that this measure of gravure quality correlates well with performance of papers in other printing processes.

The problem with printability testers based upon gravure printing is that presently available testers are precision printing presses. These testers are large for testing instruments and, while perhaps suitable as a laboratory instrument, are not suited for paper mill use by paper technicians having little printing experience. These press testers are also expensive and therefore not many mills are able to afford and maintain one.

Research to determine which fundamental qualities of paper affect printing quality suggests that something less than a printing press may be used to predict printing quality. In examining gravure prints, it was discovered that most missing dots occur on papers in local areas of low fiber density. See J. Marton, GRI Report No. M-102 (1978). Fiber density distribution within a paper's thickness over its surface area or "formation" is a well-known characteristic used by papermakers to judge the quality of their product. Formation is commonly defined as the point-to-point distribution of the physical density of the fibers (in terms of weight-per-unit volume or basis weight) of a paper sheet over its area.

In relating Marton's missing dot observation noted above to formation, analysis shows that when a uniform pressure is applied to the surface of a paper, only the least compressible (the most dense) elements of the paper structure will support the load. Compressible (or less dense) elements will give in and provide just a fraction of the total resistivity of the paper to the pressure.

Other researchers have recognized that intrinsic formation of a sheet is an important, if not the most important, property of a paper. O. Kallmes in "New Approach to Measuring Formation—A Matter of Uniformity," Paper Trade Journal, pp. 46-50 (Oct. 25, 1971) in examining a number of techniques and devices for measuring formation, noted the impact on printing of highly localized microscale variations. Kallmes concluded that the fundamental printability quality characteristic is "uniformity" of formation. He found that gravure printing quality is extremely sensitive to "uniformity" of formation, although both variation in caliper and surface smoothness contribute.

The known devices for measuring formation and relating it to printing generally measure variations in transmittance of radiation through a paper sample. They differ with respect to the type of radiation used (visible light, X-rays or beta rays) and the techniques used to transform transmittance variations into an index of formation.

In one instrument a test paper is sandwiched between a beta ray emitting film and a photographic film plate. After exposure of the film there is a negative picture of the mass distribution of the fibers over the surface examined. The exposed film is scanned by an optical microdensitometer. These results are analyzed by computer producing a basis weight histogram and various other statistics. A difficulty with this technique, which is widely recognized as producing a true image of the formation of a paper throughout its thickness, is that it is complex, costly, requires a highly trained operator and is extremely time consuming.

A number of instruments are based on measurement of transmission of a highly collimated beam of light through a paper sample. The transmitted signal is analyzed to produce a basis-weight contour map in which the higher the basis weight the heavier the shading. However, sheet opacity variations caused by surface fillers and the like interfere with results.

Another approach in quantifying the printability of papers regards surface smoothness of a paper as a primary indicator of the perfection of contact between ink and paper. These testers, commonly called smoothness testers, are often based on the measurement of the rate at which air, under a given pressure, can leak between the surface of the paper and a hard, smooth surface pressed against it. The lower the rate of leakage, the smoother the surface. A number of other smoothness testers utilize optics. Typically, the sample is pressed against a glass prism. A parallel beam of light is passed through the prism normal to the surface of the paper. Reflected light at certain angles is measured at photoelectric cells to determine the percentage of the paper surface which actually touches the prism. The percentage is by definition of this test a measure of the printing quality of the paper.

The difficulty with the radiation transmittance formation testers and the optical and air leakage smoothness instruments is that they do not duplicate the printing process conditions under which ink transfers. A principal defect is that pressures utilized, if any, are insufficient to account for the effects of typical printing pressures. A defect of instruments that do use pressure, such as air leak devices, is that they tend to average out surface voids. In printing, however, it is the individual voids which produce missing dot printing defects.

Those instruments which are correlatable with printing all require a great deal of skill to operate to produce consistent results. None of the instruments available today are truly suitable for use in the mill by paper lab technicians.

As a consequence today, while papermakers recognize that formation is a fundamental quality of their product, they are unable to find a testing apparatus and procedure which is suitable for the mill environment with respect to either cost, timeliness or reproducibility. The present tests used in the mill tend to be purely subjective. In one typical test, for example, a specimen is viewed on a light box and its highlighted pattern is compared with control papers. This test is, of course, difficult to reproduce or replicate between testing technicians.

SUMMARY OF THE INVENTION

The method and apparatus of the invention requires advancing a solid elongated marker over the surface of a fibrous sheet to be analyzed for formation and surface characteristics. The marker exerts a pressure on the sheet of a magnitude selected to develop or emphasize a particular character of interest. Where paper printability is of interest, the pressure is selected to substantially duplicate what a paper experiences in printing and transfer.

The marker may be any material which when advanced across the sheet produces an image whose intensity is proportional to the local pressures exerted upon it. Hence, while graphite is preferred, any material which produces a similar image is suitable. Where an image in a digital form is required, a piezoelectric matrix may be used.

It is an object of this invention to provide a simple, yet accurate and reproducible method and apparatus suitable for use by mill technicians to evaluate the formation and surface properties of papers, and in particular, to predict a paper's suitability for use in printing.

The apparatus of the invention produces a thin graphite layer on a paper sample in the form of an image which is directly related to the fundamental paper characteristics which affect a paper's performance in ultimate use, including for printing. The graphite image is related to the formation, smoothness and conformability qualities of the paper sheets.

The apparatus includes a base for supporting a paper sample to be tested. A marker, typically a block of graphite, rests in contact with the paper sample. A load or pressure is applied to the graphite marker exerting a normal force on a paper of sufficient magnitude to simulate printing process pressures. The marker, under load, is then advanced over the surface of the test paper, producing a graphite image which is correlatable with the physical distribution of the pulp fibers in the sheet over that portion of the sheet contacted.

The base material may be chosen to substantially duplicate typical materials which support the paper web in printing processes. A rigid base emphasizes formation. A rubber-like flexible surface may be used, producing a graphite image which largely reflects and emphasizes the surface smoothness and, when compared with the formation image, "conformability" or printing flexibility of the sheet.

The resulting graphite image is subjected to further measurement to directly correlate the image with some desired paper quality. For example, the graphite analyzer produces images which can be used to predict the capability of the paper to produce gravure prints. Gravure quality of a paper can be predicted by measuring the unmarked areas of the graphite image. Such results are directly correlatable with the well-known gravure test of printing quality wherein the number of missing dots of the print image are counted.

The missing dot count value may be compared with missing dot counts of standard quality printed papers. Such a comparison permits predicting how tested papers will perform in gravure printing in comparison with standard papers.

DESCRIPTION OF THE PREFERRED EMBODIMENTS

The structural and surface properties tester for paper or formation-surface tester of this invention and its method of use are based upon the definition of "formation" as the point-to-point distribution of the physical density (mass or basis weight) of a paper sheet over its area. When a uniform pressure is applied to the surface of the paper, only the least compressible or most dense elements of the internal paper structure will support the load. The more compressible elements will give in and provide just a fraction of the general total resistivity of the paper to the pressure.

Figure 1:
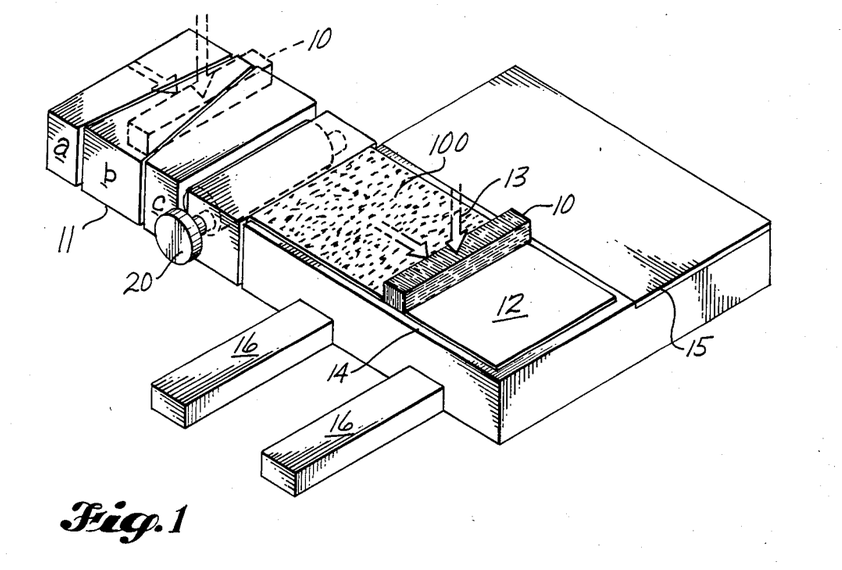
FIG. 1 shows a method of characterizing paper formation.
Figure 2:
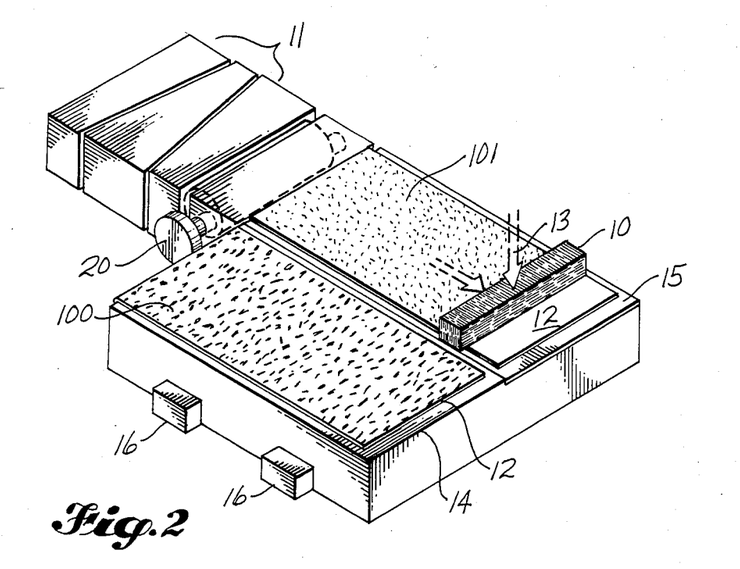
FIG. 2 shows a method of characterizing surface smoothness of paper.

Referring to FIGS. 1 and 2, the method of the invention employs a graphite marker 10, advancing first across a sharpener 11 and thence into contact with the paper sample 12 to be tested which is fixed to and supported on a backing 14. The marker, while in contact with the paper, is subjected to a load 13 such that the marker exerts a uniform normal pressure on the area of the paper to be marked. The graphite marker imparts a thin layer of graphite over the paper sample surface producing an image that is related to the fundamental paper qualities of internal formation and surface smoothness. As expected, the image comprises a multiplicity of areas of different degrees of darkness along with a number of areas that are unmarked. The number of chips separating from the graphite is proportional to the pressure distribution among local points of contact.

Figure 3:
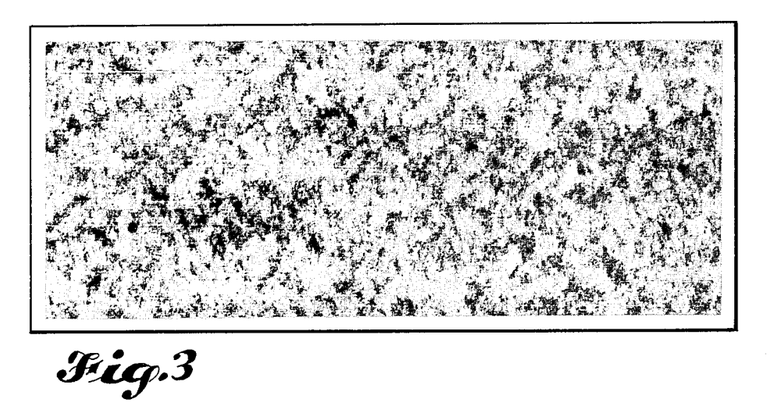
FIG. 3 is an image produced by a paper using the method of FIG. 1.

The method employs a rigid backing 14, generally steel, for supporting the paper sample where the intent of the test is to examine internal structure of the paper. The resulting image 100 is shown in FIG. 3 in which the intensity of the markings reflects the more incompressible or denser areas of the paper.

Figure 4:
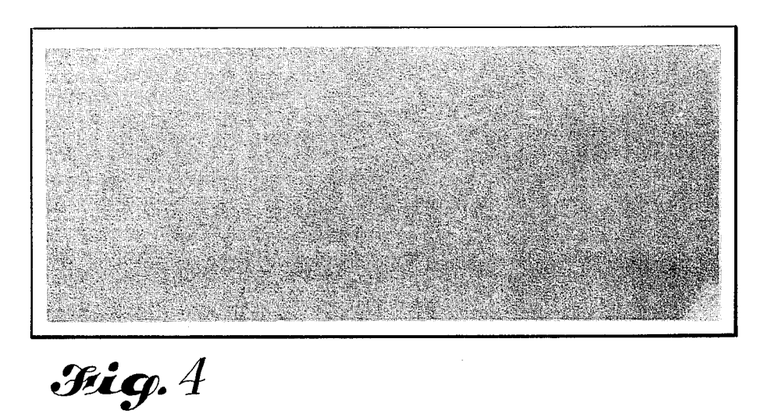
FIG. 4 is an image produced by a paper using the method of FIG. 2.
Figure 5:
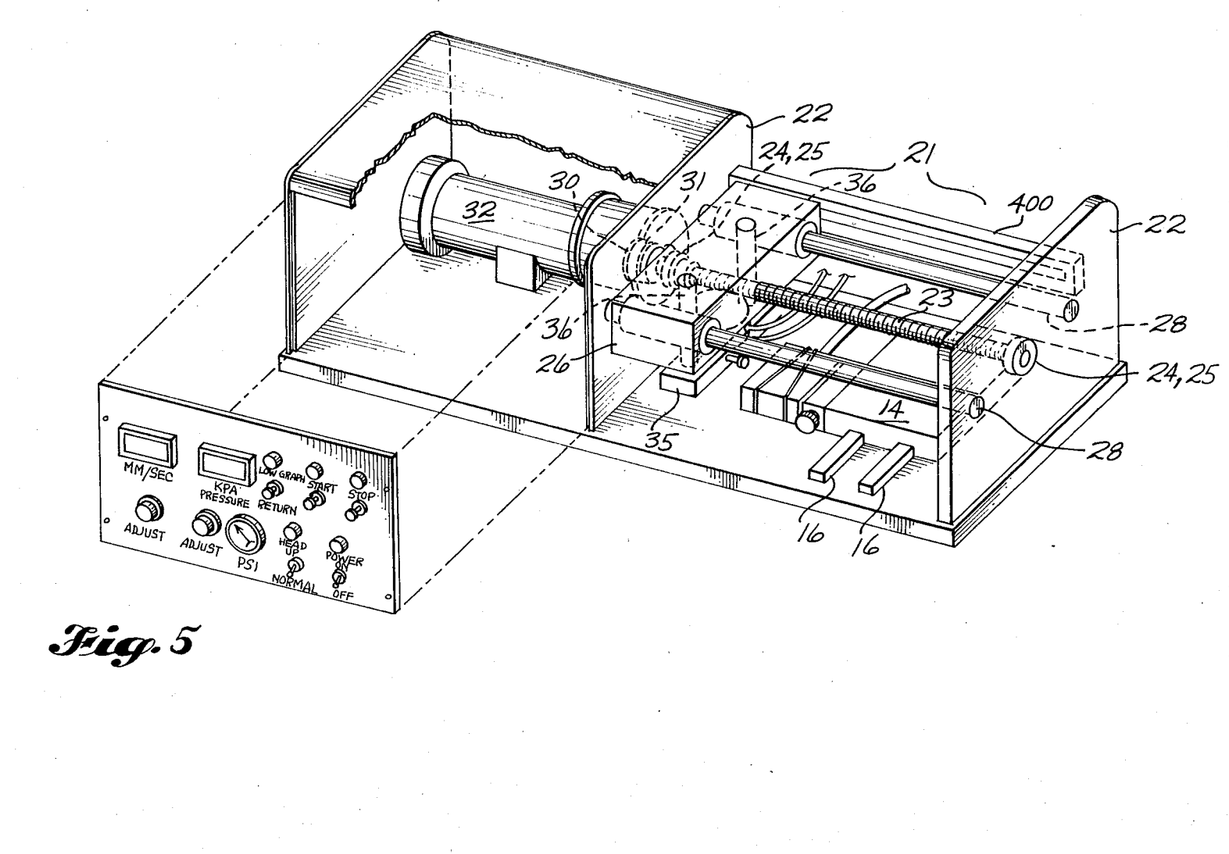
FIG. 5 is a view of a preferred embodiment of the formation-surface paper tester of this invention.
Figure 6:
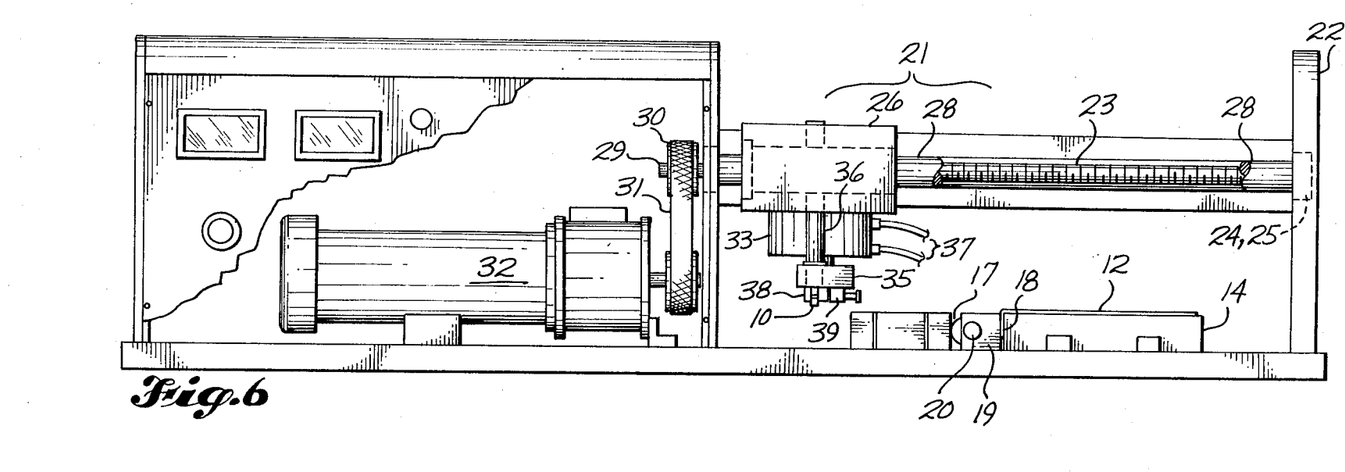
FIG. 6 is an elevational schematic view of the principal features of the tester.
Figure 7:
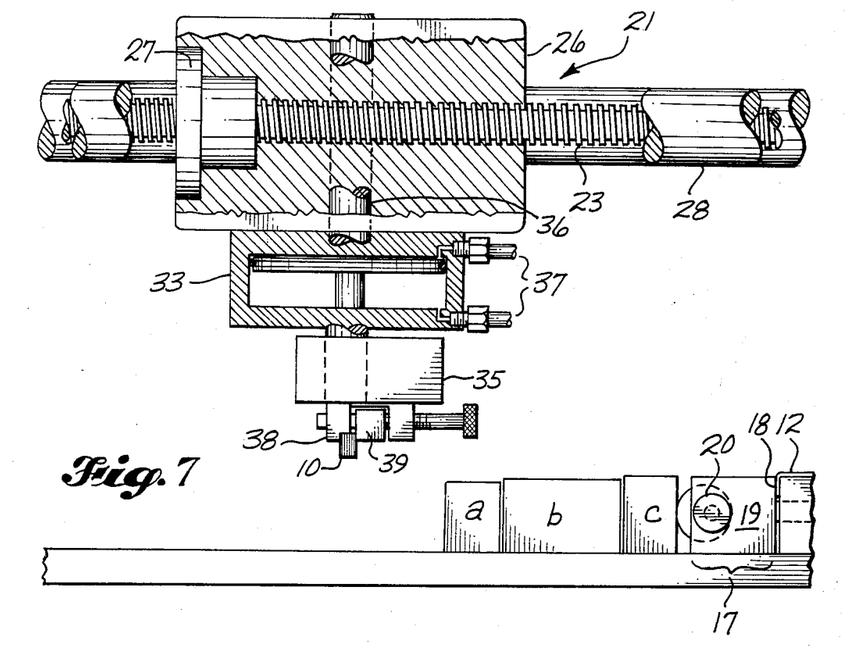
FIG. 7 shows tester positioning of the graphite marker.
Figure 8:
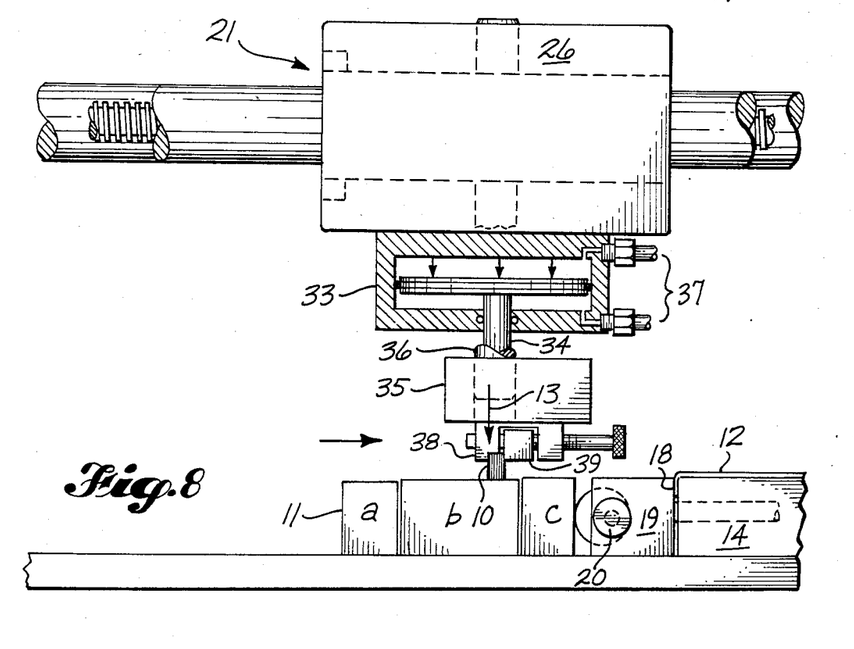
FIG. 8 shows the graphite marker as it travels over a sharpener/conditioner prior to contact with the test paper.

The method employs a flexible backing 15, generally a rubber composition blanket, for supporting the test paper where the intent of the test is to examine surface smoothness or other surface detail. FIG. 4 shows an image 101 produced on the same paper 12 of FIG. 3 when a flexible backing is used. When a flexible backing is used between the paper and the base, a finer scale image is produced. The nonuniform pressure distribution is compensated by local flexing of the backing resulting in a more uniform graphite print. The flexible backed prints emphasize surface smoothness characteristics and the "conformability" of the paper. Conformability is an interaction of formation and smoothness reflecting the element of pressure in the testing process. With respect to printability, for example, conformability suggests how a paper makes up for surface and formation imperfections by flexing or flowing in response to printing loads.

It is usually desirable to make both formation and surface characteristic prints of test papers. This is particularly true when examining printing papers where the conformability of a paper is to be assessed. Conformability information is obtained by comparing the formation and surface effects images. The two backings are slidably mounted on rails 16. After first printing on the rigid backing, the flexible backing plate 15 is slid into place along rails 16 for a surface effects print to be made on another sample of the test paper. Thus, for most tests both prints, one each similar to FIGS. 3 and 4, are made. The blanket material may be of any flexible composition. It is selected to emphasize the particular paper characteristic under consideration. When printability is of interest, the material is generally selected to match the surface of a printing impression roll.

Referring to FIGS. 5-8, the preferred apparatus is shown in schematic views. The paper sample 12 to be tested is mounted upon a supporting base, here rigid surface 14. A clamping mechanism 17 secures the test paper 12 on the base by clamping paper leading edge 18. Movable clamp element 19 is urged against the base 14 by cam operator 20 holding the paper edge 18 and hence the rest of the paper sample 12 securely onto the base 14.

Graphite marker 10 is positioned with respect to the test paper 12 by a mechanism 21 which permits the marker to graphitize the test papers under uniform conditions of pressure and speed.

Bulkheads 22 support a threaded rod 23, commonly called an acme screw, horizontally mounted in thrust and conventional bearings 24, 25. A carriage block 26 secures a nut 27 which threads screw 23. A pair of stabilizer rods 28, spaced apart in parallel on the same plane as the screw, pass through the carriage block and are fixed to bulkheads 22.

Figure 9:
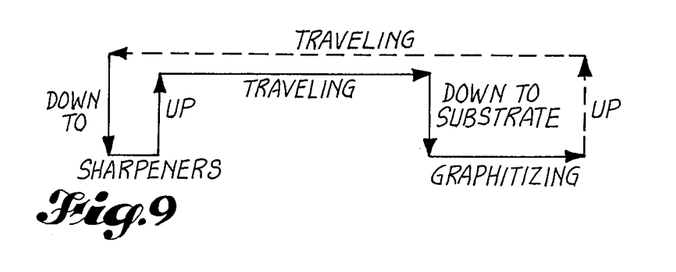
FIG. 9 shows a preferred path of travel of the graphite marker in an imaging sequence.

The arrangement is such that upon rotation of screw 23, carriage block 26 travels along the screw 23 and stabilizer rods 28 in a horizontal direction. Shaft 29 of screw 23 is fitted with a pulley 30 and connected by belts 31 to a motor 32 capable of precisely advancing or reversing the screw direction depending upon the graphite printing sequence desired. A programmable controller (not shown) directs the motor operation to follow the sequence of test operations shown in FIG. 9. A noncontact limit switch system 400 is an element of the control system.

A double acting short stroke air cylinder 33 is fastened to carrier 26. The piston rod 34 of the cylinder 33 is attached to a graphite holder head 35. The head 35 is stabilized for vertical movement in response to the cylinder actuation by two vertical stabilizing rods 36 arranged in parallel. The stroke of the cylinder is such, when air pressure is supplied through line 37 to the cylinder 33, the graphite bar 10 may be brought into contact with the sharpener 11 and thence into contact with the test paper 12, exerting an adjustable normal pressure on the paper. The cylinder 33 causes the graphite bar 10 to exert a pressure on the test paper substantially similar in effect to those pressures utilized in printing, for example. Typical cylinder pressures are up to 30 psi (210 kPa).

A graphite clamping mechanism 38 is pivotably attached to head 35 so that forces exerted upon it by cylinder 33 are translated into the graphite bar being uniformly pressed into contact with the test paper. A spring clamp 39 holds the graphite bar 10 in the clamping mechanism.

In operation, a test paper 12 is clamped in place on the base, selecting either the rigid 14 or flexible 15 surfaces depending upon the intent of the observation. A graphite marker bar 10 is inserted in the marker clamping mechanism 39. Actuation of the motor 32 causes the sequence of events shown in FIG. 9 under the direction of the programmable controller (not shown) to occur.

In dragging a graphite marker across the paper substrate, tiny flat chips of graphite are left on the paper surface. The number of chips separating from the graphite is proportional to the pressure exerted on the paper sandwiched between the rigid effects of the air cylinder and base. The paper sample variations in density cause areas of high and lower pressure to be exerted on the graphite, resulting in a print on the paper showing the more dense paper areas. Excess chips are vacuumed from the sharpener.

The amount of chip separation and marking of the paper is also dependent upon speed of the graphite riding on the paper surface. This variation is eliminated from this embodiment of the invention by fixing the speed at one value for all tests so that different papers may be compared. A speed range of between 0–100 mm/second, preferably 0–60 mm/second, provides acceptable performance. The invention is not speed limited, however. Speed may sometimes be altered to better develop an image to emphasize some particular characteristic of a paper being tested.

Equally important, the quality of the graphitized print produced is dependent upon the surface smoothness of the graphite marker applied to the paper. This variable is substantially eliminated from the test by conditioning the graphite before each printing by directing the graphite bar to travel across the sharpener 11. The sharpener includes three plate elements, a, b and c on FIG. 1 having highly polished mirror-like surfaces, each of which, in the direction of travel, is slightly higher than the preceding element. As a result of traveling across the sharpener, the graphite bar attains a fresh essentially planar, near mirror-like surface before each test, having substantially the surface polish of the sharpener elements.

The pressure which the graphite exerts on the paper to be graphitized is an important controllable variable of the test method and apparatus. The intent of selecting a pressure is to use pressures which produce impacts on the method of a magnitude which emphasizes the characteristic desired to be examined. As an example, where the test is designed to predict printability of a paper, a pressure may be selected which substantially duplicates the impact of pressure in commercial printing. Pressures on the order of 1–5 kg/cm$^2$ are utilized successfully for such tests in comparison with actual printing pressures on the order of 10–50 kg/cm$^2$ in printing quality tests.

Figure 10:
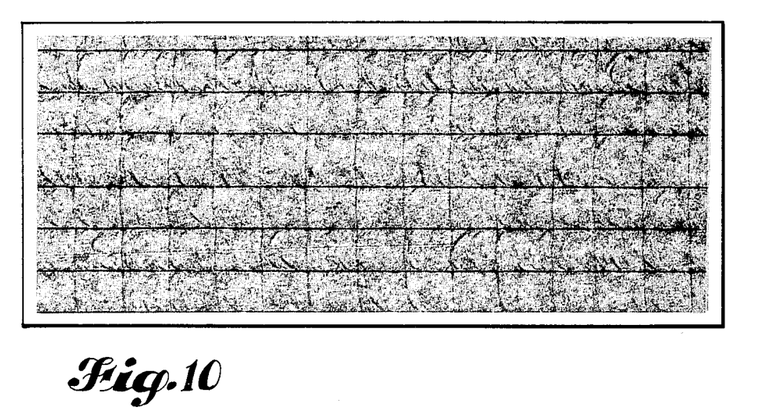
FIG. 10 is a graphite print of a paper sample showing internal structure.
Figure 11:
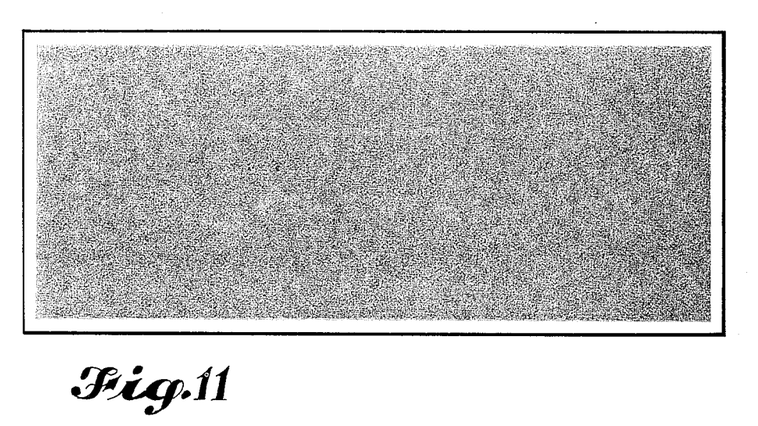
FIG. 11 is a graphite print of a paper sample showing surface markings.

Examples of graphite prints produced by the method and apparatus of the invention are shown in FIGS. 10 and 11. The two prints shown suggest the usefulness of the invention in evaluating process effects and product qualities.

FIG. 10 is a print of a paper towel product which includes an internal reinforcing nylon netting. The print clearly shows the presence and pattern of the reinforcing material which details would not be determinable from viewing a sample of the towelling alone.

FIG. 11 is a print of a paper sheet using the flexible backing so that mainly surface topography of the paper sheet is shown. FIG. 11 shows a "knuckle" pattern imprinted on a paper surface as a result of a particular couch roll felt. Such a print is useful in evaluating pressing and dewatering processes.

Foreign intrusions such as surface contaminants can be developed on graphitized prints. Wrinkles and other mechanical defects are revealed likewise. A print showing point-to-point distribution of the wood fibers internally is useful in predicting tensile strength and can predict a potential failure condition where the manufacturing process repeatedly imparts lines of low fiber density across or along a sheet as a result of some process irregularity.

Another useful application of the tester is in predicting power requirements for fiberizing a dry pulp sheet for fluff pulp uses such as in diapers. A formation print of a dry pulp sheet shows the agglomerated clumps or fibers or "knots" distributed in a sheet. The number of these clumps per unit areas for a number of standard pulps, are correlated with the power requirements to fiberize the dried sheets. The formation print of a sheet to be tested is compared with these standards and the power requirement for fiberization is predicted. If the predicted power requirements are too high, steps are taken in the pulping or sheet-making process to change formation, for example.

A principal use of the graphitized prints is in predicting the printing quality or printability of a paper, as discussed above in the background of the invention. The graphite prints produce "pictures" of internal formation and surface smoothness, well-known printing paper qualities. Most uniquely, the graphite prints reflect the ability of the paper to flex in response to printing pressures and printing equipment parameters such as flexible printing rolls. Thus, the graphitized tester produces prints much like the printing processes which employ pressure, which prints are especially useful in predicting print quality for any printing technique involving pressure contact between the printing plates and the paper to effect ink transfer. As noted above, the printability of a paper may be predicted or compared with another paper by treating the graphitized print as if it were a gravure print. Such prints are easily evaluated in terms of a missing dot count or other techniques as described in the example below.

EXAMPLE

Graphite prints of five printing papers, characterized as follows, were made: (1) borderline, envelope; (2) 55 lb envelope white wove; (3) envelope; (4) 60 lb Husky; offset wove; and (5) 60 lb Husky; regular offset. "Husky" is a registered trademark of Weyerhaeuser Company, Taccoma, Wash., for printing and offset papers. The graphite prints were analyzed by the following method:

A ratio of the number of dots which were not graphitized to the total number of dots viewed was determined. A template with 100 apertures or "dots" 1 mm in diameter was employed. Each print was examined mounted on a light box under a seven power magnifying glass.

Gravure prints of the test papers were made on a Prufbau Rotogravure Printability Tester, manufactured by Profbau Gmbh., of Peissenberg/München, Germany. The missing dot count and related ratios were determined by microscopically examining the prints and actually counting each missing dot.

The resulting evaluations of the five test papers produced by the graphite tester of this invention and the Prufbau printability tester were compared. The graphitized evaluations, using the template missing dot count method of analyzing the graphitized prints correlates substantially with the Prufbau evaluations. Perfection of the template technique by altering the pattern and dot sizes produces results which correlate substantially perfectly with the Profbau tests.

Where very different papers are to be compared, the effect of abrasiveness variation between the papers can be eliminated by use of a thin white polyethylene film overlaying the test paper. The graphitized print is made on the polyethylene film. The film is extremely conformable and for practical purposes produces an identical reproduction of the density distribution of the paper.

Figure 12:
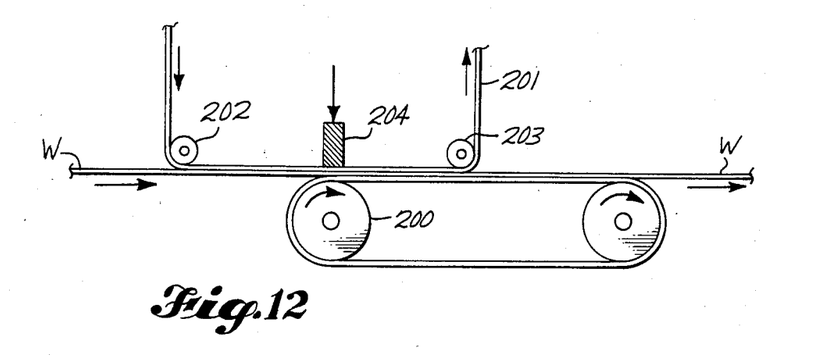
FIG. 12 is an embodiment showing production of an image from a moving paper web.

The film technique is also useful when the instrument is employed as an on-line paper tester. FIG. 12 shows such an arrangement. A paper web W travels into contact with a paper roll 200. A film 201 on which the image is to be recorded is driven at a velocity equal to that of the paper web W.

Rollers 202, 203 urge the film into contact with the moving paper web W. A graphite marker 204 is urged into contact with the film, exerting sufficient pressure on the paper to duplicate printing effects, producing the graphited images of the invention on the conformable film.

Figure 13:
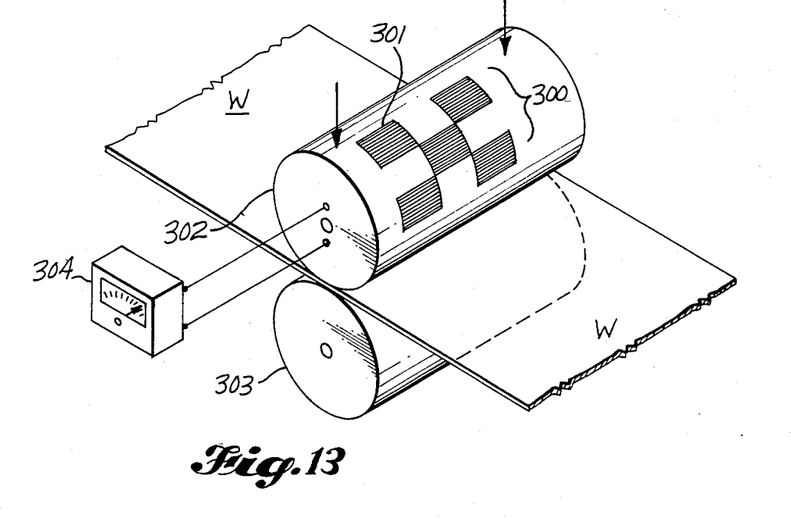
FIG. 13 is an embodiment of the invention showing production of a formation-surface image using a matrix of piezoelectric sensors.

While the preferred embodiment employs a graphite block as a marker, the method and apparatus of the invention are not limited to graphite. Any instrument which is sensitive to pressure variation can be used in place of the graphite marker where the resulting output in intensity is proportional to pressure. Where a visual image is to be produced, chalk, pastels, charcoal, crayon or similar pigmented wax product and the like may be used. Basically any marker which can provide contrast between areas of high and low pressure may be used.

Where a nonvisual image is useful, for example, an image that is in digital form for convenience of analysis, the marker is a piezoelectric element such as a quartz-based sensor. As shown in FIG. 13, a matrix 300 of these sensors 301 are fixed to a roll 302 which is urged into contact with an opposing roll 303 so that web W experiences, for example, printing pressures. The matrix is designed to report pressure variation results to a processing unit 304 which may display an image or otherwise utilizes the formation-surface data.

I claim:

1. A method of evaluating the internal structure and surface properties of a sheet material which comprises:
   securing a sample of the sheet material to a supporting means;
   providing a solid marker means having an elongated sample contacting surface adapted to transfer a visible marking to any portion of the sample surface contacted by the means;
   conditioning the sample contacting surface of the solid marker means prior to contacting the sample in order to remove any surface-irregularities;
   providing a loading means so that the marker means will bear against the sample with a predetermined pressure;
   contacting the sample with the marker means;
   uniformly advancing the conditioned marker means across the sample while under said pressure so that the marker means contacts and marks a substantial portion of the sample surface; and
   relating the pattern of markings on the sample surface to the property being determined.

2. The method of claim 1 which further includes conditioning the sample contacting surface of the marker means to a planar, near mirror-like quality prior to contacting the sample.

3. The method of claim 2 in which the image intensity of the marked portions is proportional to localized pressures between the sample and the conditioned marker means.

4. The method of claim 3 in which the fibrous sheet material is paper.

5. The method of claim 4 in which the property being evaluated is formation and which further comprises providing a rigid supporting means and selecting a pressure so as to mark localized areas of highest density while not marking areas of relatively lower density, or marking the higher density areas with a higher intensity image than the lower density areas, whereby said markings are related to the mass distribution of the fiber within the paper.

6. The method of claim 4 in which the property being evaluated is surface smoothness and which further comprises providing a resilient supporting means comformable to the sample when the conditioned marker means is advanced across the sample whereby the markings made on the sample are related principally to fine surface topography.

7. The method of claim 4 wherein the pressure is selected to simulate the effect of pressures encountered in commercial printing processes.

8. The method of claim 7 in which the pressure is within the range 1–5 kg/cm$^2$.

9. The method of claim 1 in which the marker material is chosen from the group of graphite, chalk, pastel, charcoal, and pigmented wax.

10. The method of claim 9 in which the marker material is graphite.

11. The method of claim 1 which further comprises interposing a flexible film between the marker means and sheet material sample so that the marked image is formed on the film rather than the sample.

12. The method of claim 11 in which the flexible film is pigmented polyethylene.

13. The method of claim 1 which further includes evaluating the property being measured by placing a grid means on selected areas of the sample surface and counting the marked and unmarked areas.

14. The method of claim 11 which further includes evaluating the property being measured by placing a grid means on selected areas of the sample surface and counting the marked and unmarked areas.

15. Apparatus for evaluating the internal structure and surface properties of a sheet material which comprises:
    a base means for supporting a sample of the sheet material;
    a solid marker means having an elongated sample contacting portion adapted for marking a substantial area of the sample surface;
    conditioning means to remove any irregularities from the sample contacting surface of the marker means;
    loading means for exerting a predetermined uniform pressure on the marker means while in contact with the sample surface; and
    traversing means for advancing the marker means so that the marker means is first lowered from a disengaged position over the conditioning means and conditioned, then raised and moved over the sample supporting area of the base means, then lowered onto the sample and moved across the sample at a predetermined pressure and uniform rate of speed while under load so as to mark a substantial area of the sample surface and produce an image on said surface relatable to the surface or internal structural properties of the sheet material.

16. The apparatus of claim 15 in which the traversing means is further adapted to raise the marker means from the sample after the sample has been marked and return said marker means to a disengaged position over the conditioning means at which position it is ready to repeat the cycle.

17. The apparatus of claim 16 in which the loading means is a pneumatic cylinder and the action of the loading means and traversing means is controlled by a programmable controller.

18. The apparatus of claim 15 in which the base means is a rigid material whereby an image is produced on a sample which is related primarily to formation or mass distribution of material within the sample.

19. The apparatus of claim 15 in which the base means is a resilient material whereby an image is produced on a sample which is primarily related to surface smoothness or fine surface topography.

20. The apparatus of claim 15 in which a base means of rigid material and a base means of resilient material are slidably mounted side-by-side on rails oriented normal to the direction of travel of the marking means so that one or the other base means may be positioned in the path of the marker means before it is advanced across the sample.

21. The apparatus of claim 15 in which the marker means has a graphite marking surface.

22. The apparatus of claim 21 in which the conditioning means is adapted to prepare the sample contacting portion of the graphite to a planar surface of near mirror-like quality.

* * * * *

UNITED STATES PATENT AND TRADEMARK OFFICE
CERTIFICATE OF CORRECTION

PATENT NO. : 4,541,273

DATED : Sep. 17, 1985

INVENTOR(S) : Yuri A. Bery

It is certified that error appears in the above—identified patent and that said Letters Patent is hereby corrected as shown below:

In column 1, line 14, "by" should read --for--;

*Signed and Sealed this*

*Seventeenth* Day of *December 1985*

[SEAL]

*Attest:*

DONALD J. QUIGG

*Attesting Officer*    *Commissioner of Patents and Trademarks*